USOO5635473A

United States Patent [19]
Lee et al.

[11] Patent Number: 5,635,473
[45] Date of Patent: Jun. 3, 1997

[54] INHIBITOR OF HEPATITIS B VIRUS REPLICATION

[75] Inventors: Hyun-Sook Lee; Yung-Dae Yun, both of Seoul; Hong-Mo Moon, Seongnem, all of Rep. of Korea

[73] Assignee: Mogam Biotechnology Research Institute, Kyonggi-Do, Rep. of Korea

[21] Appl. No.: 347,343

[22] PCT Filed: Oct. 12, 1994

[86] PCT No.: PCT/KR94/00136

§ 371 Date: Apr. 24, 1995

§ 102(e) Date: Apr. 24, 1995

[87] PCT Pub. No.: WO96/11017

PCT Pub. Date: Apr. 18, 1996

[30] Foreign Application Priority Data

Oct. 7, 1994 [KR] Rep. of Korea ............... 94-25752

[51] Int. Cl.$^6$ .................................................. C07K 14/82
[52] U.S. Cl. ................................................ 514/2; 530/350
[58] Field of Search ........................... 530/350; 514/2

[56] References Cited

PUBLICATIONS

D. Ganem et al., The Molecular Biology of The Hepatitis B Viruses, Ann. Rev. Biochem., 56:651–693 (1987).
C.H. Yuh et al., Transciptional Regulation of Precore and Pregenomic RNAs of Hepatitis B Virus, J. Virol., 66(7):4073–4084 (1992).
T.K. Antonucci et al., Hepatitis B Virus(HBV) Promoters Are Regulated by the HBV Enhancer in a Tissue-Specific Manner, J. Virol., 63(2):579–583(1989).
G.H. Wang et al., The Reverse Transcriptase of Heptatis B Virus Acts As a Protein Primer for Viral DNA Synthesis, Cell, 71:663–670(1992).
G.H. Wang et al., Novel Mechanism for Reverse Transcription in Hepatitis B Viruses, J. Virol., 67(11):6507–6512(1993).
P. Tiollais et al., The Hepatitis B Virus, Nature, 317:489–495(1985).
D.S. Chen, From Hepatitis to Hepatoma: Lessons from Type B Viral Hepatitis, Science, 262:369–370(1993).
D.P. Lane et al., T Antigen is Bound to a Host Protein in SV40-Transformed Cells, Nature, 278:261–263(1979).
M. Hollstein et al., p53 Mutations in Human Cancers, Science, 253:49–53(1991).
S.E. Kern et al., Identification of p53 as a Sequence-Specific DNA-Binding Protein, Science, 252:1708–1711(1991).
E. Seto et al., Wild-type p53 Binds to the TATA-Binding Protein and Represses Transcription, Proc. Natl. Acad. Sci., USA, 89:12028–12032(1992).
R. Truant et al., Direct Interaction Between the Transcriptional Activation Domain of Human p53 and the TATA Box-Binding Protein, J. Biol. Chem., 268(4):2284–2287(1993).

N. Ragimov et al., Wild-type but not Mutant p53 can Repress Transcription initiation in vitro by Interfering with the Binding of Basal Transcription Factors to the TATA Motif, Oncogene, 8:1183–1193(1993).
D.W. Martin et al., p53 Binds to the TATA-Binding Protein-TATA Complex, J. Biol. Chem., 268(18):13062–13067(1993).
S. N. Agoff et al., Regulation of the Human hsp70 Promoter by p53, Science, 259:84–87(1993).
P. Sarnow et al., Adenovirus Elb–58kd Tumor Antigen and SV40 Large Tumor Antigen Are Physically Associated with the Same 54kd Cellular Protein in Transformed Cells, Cell, 28:387–394(1982).
L. Szekely et al., EBNA–5, an Epstein-Barr Virus-Encoded Nuclear Antigen, Binds to the Retinoblastoma and p53 Proteins, Proc. Natl. Acad. Sci., USA, 90:5455–5459(1993).
P.N. Friedman et al., Wild-type, but not Mutant, Human p53 Proteins Inhibit the Replication activities of Simian Virus 40 Large Tumor Antigen, Proc. Natl. Acad. Sci., USA, 87:9275–9279(1990).
S. Hosono et al., Molecular Analysis of the p53 Alleles in Primary Hepatocellular Carcinomas and Cell Lines, Oncogene, 6:237–243(1991).
P. Jackson et al., Wild-type Mouse p53 Down-Regulates Transcription from Different Virus Enhancer/Promoters, Oncogene, 8:589–597(1993).
D.P. Aden et al., Controlled synthesis of HBsAg in a Differentiated Human Liver Carcinoma-Derived Cell Line, Nature, 282:615–616(1979).
A. Puisieux et al., Retinoblastoma and p53 Tumor Suppressor Genes in Human Hepatoma Cell Lines, FASEB., 7: 1407–1413 (1993).
H. Will et al., Replication Strategy of Human Hepatitis B Virus, J. Virol., 61(3):904–911(1987).
K. Yaginuma et al., Identification of a Promoter Region for 3.6–Kilobase MRNA of Hepatitis B Virus and Specific Cellular Binding Protein, J. Virol., 63(7):2914–2920(1989).
R. Zakut-Houri et al., Human p53 Cellular Tumor Antigen: cDNA sequence and Expression in COS Cells, EMBO. J., 4(5):1251–1255(1985).

(List continued on next page.)

*Primary Examiner*—Robert A. Wax
*Assistant Examiner*—K. Cochrane Carlson
*Attorney, Agent, or Firm*—Darby & Darby, P.C.

[57] ABSTRACT

The present invention relates to a novel use of a biologically active protein, p53 as an inhibitor of hepatitis B virus(HBV) replication. The inhibitory role of p53 on HBV replication was assessed by the reduced levels of three different markers, i.e., HBsAg and HBc/eAg secreted into the medium, HBV DNA, and RNAs. Based on the above results, it was concluded that wild-type p53 specifically represses the activity of pregenomic/core promoter of HBV and inhibits the replication of HBV by down-regulation of the pregenomic/core promoter. Therefore, the present invention provides a novel use of protein p53 as a HBV replication inhibitor which can be developed into an agent for the treatment of acute/chronic hapatitis and prevention of liver cirrhosis and hepatocellular carcinoma(HCC) caused by HBV.

3 Claims, 11 Drawing Sheets

OTHER PUBLICATIONS

T. A. Kunkel, Rapid and Efficient Site–Specific Mutagenesis Without Phenotype Selection, Proc. Natl. Acad. Sci., USA, 82:488–492(1985).

A.C. Johnson et al., Epidermal Growth Factor Receptor Gene Promoter, J. Biol. Chem., 263(12);5693–5699(1983).

Y. Shaul et al., A Human Hepatitis B Viral Enhancer Element, EMBO. J.., 4(2):427–430(1985).

A.K. Raney et al., Differentiation–Specific Transcriptional Regulation of the Hepatitis B Virus Large Surface Antigen Gene in Human Hepatoma Cell Lines, J. Virol., 64(5):2360–2368(1990).

B.E. Blum et al., Heptatis B Virus X Protein is Not Central to the Viral Life Cycle, J. Virol., 66(2):1223–1227(1992).

K. Yaginuma et al., Hepatitis B Virus(HBV) Particles are Produced in a Cell Culture System by Transient Expression of Transfected HBV DNA,Proc. Natl. Acad. Sci., USA, 84: 2678–2682(1987).

J.R. Sanes et al., Use of a Recombinant Retrovirus to Study Post–Implantation Cell Lineage in Mouse Embryos, EMBO. J., 5(12):3133–3142(1986).

Wang et al. 1994 PNAS 91:2230–2234.

Dutta et al 1993 Nature 365: 79–82.

Subler et al 1992 J Virol 66:4757–4762.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: cDNA to mRNA     ( v i ) ORIGINAL SOURCE:
        ( A ) ORGANISM: Hepatitis B virus     ( v i i ) IMMEDIATE SOURCE:
        ( B ) CLONE: Seq.Id.No.1

( x i ) SEQUENCE DESCRIPTION: SEQ ID NO:1:

CACCCCGCC  CGTCACCCGC  GTC         2 3

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: cDNA to mRNA ( v i ) ORIGINAL SOURCE:
  ( A ) ORGANISM: Hepatitis B Virus ( v i i ) IMMEDIATE SOURCE:
  ( B ) CLONE: Seq.Id.No.2

( x i ) SEQUENCE DESCRIPTION: SEQ ID NO:2:

GCTTTGAGGT GCTTGTTTGT GCC 23

INHIBITOR OF HEPATITIS B VIRUS REPLICATION

BACKGROUND OF THE INVENTION

1. Field of the Invention

The present invention relates to a novel use of a biologically active protein, more specifically, to a novel use of protein p53 as an inhibitor of hepatitis B virus replication.

2. Description of the Prior Art

Hepatitis B virus(hereinafter referred to as 'HBV'), a causative agent of acute/chronic hepatitis, consists of a partially double-stranded 3.2 kb circular DNA and from which, four proteins are synthesized: they are the core, polymerase, surface antigen and X-gene product(see: Ganem, D. and Varmus, H. E., Annu. Rev. Biochem., 56: 651–693 (1987)).

Four promoters with unique functions have been identified in HBV genome. The pregenomic/core promoter directs the synthesis of 3.6 kb mRNA which contains all the genetic information encoded by the virus. This RNA serves as a replication intermediate and as a template for the synthesis of core and polymerase(see: Seeger, C. et al., Science, 232: 477–484(1986); Yuh, C. H. et al., J. Virol., 66:4073–4084 (1992)). The S promoter and the pre-S promoter direct the synthesis of 2.1 and 2.4 kb RNAs utilized for the generation of pre-S1, pre-S2, and S proteins. X promoter directs the transcription of 0.9 kb RNA specific for the synthesis of X gene product. Liver-specific and differentiation state-specific utilization of these promoters are regulated by the two enhancer elements, i.e., enhancer I(ENI) and enhancer II(ENII). These enhancers along with HNF-1(hepatocyte nuclear factor-1) binding element are largely responsible for the restricted tropism of HBV to hepatocytes(see: Antonucci, T. K. and Rutter, W. J., J. Virol., 63:579–583 (1989)).

The mechanism of HBV replication differs from that of other DNA viruses in that, like retroviruses, the reverse transcription step is involved. Upon infection of the hepatocytes, a partially double-stranded genome is converted to a complete double-stranded circular, supercoiled DNA. Employing this as a template, 3.6 kb RNA, which is called the pregenome, is transcribed. The pregenome is packaged into a nucleocapsid and is reverse-transcribed using polymerase as an initiation primer(see: Wang, G. H. and Seeger, C., Cell, 71:663–670(1992); Wang, G. H. and Seeger, C., J. Virol., 67:6507–6512(1993)) to generate the minus-strand, single-stranded DNA. The polymerization of the second strand follows until approximately half of the genome is synthesized, resulting in the generation of partially double-stranded circular genome, which is coated and secreted by the infected cells(see: Tiollais, P. et al., Nature, 317:489–495(1985); Ganem, D. and Varmus, H. E., Annu. Rev. Biochem., 56:651–693(1987)).

Despite extensive epidemiological evidences that chronic carriers of HBV have an increased risk of developing hepatocellular carcinoma(hereinafter referred to as 'HCC') (see: Beasley, R. P. et al., Lancet ii, 1129–1133(1981)), the exact mechanism by which HBV cause HCC still remains unclear. Although integration of HBV DNA into the host chromosome is observed in cancer patients, integration appears to occur at random sites rendering it unlikely that integration-mediated alteration of adjacent gene expression is the cause of HCC(See: Chen, D. S., Nature, 262:369–370 (1993)).

On the other hand, p53, a 53 kDa protein ubiquitous in mammalian cell, was reported to have the function of tumor suppressors. It was first isolated as a coprecipitated form with SV40 large tumor antigen(see: Lane, D. P. and Crawford, L. V., Nature, 278:261–263(1979); Linzer, D. I. H. and Levine, A. J., Cell, 7:43–52(1979)), and its biological function and biochemical properties have been further investigated with the aid of molecular biology, e.g., cDNA cloning of p53 in various organisms. It has been also reported that mutation in p53 tumor suppressor gene is the most frequently occurring event in a wide variety of human tumors(see: Hollstein, M. et al., Science, 253:49–53(1991)). However, the precise mechanism how p53 exerts its tumor suppressing function is not yet clear, except for recent reports suggesting that at least one function of p53 lies in the regulation of transcription.

p53 acts both as a transcription activator and the transcriptional repressor. When working as a transcriptional activator, p53 binds to the enhancer element in a sequence-specific manner(see: Kern, S. E. et al., Science, 252:1707–1711(1991)) and presumably interacts with the basic transcriptional machinery. In case p53 mediates transcriptional repression, p53 forms a complex with the proteins of the basic transcriptional machinery like TATA-box binding protein(see: Seto, E. et al., Proc. Natl. Acad. Sci., USA, 89:12028–12032(1992); Truant, R. et al., J. Biol. Chem., 268:2284–2287(1993); Ragimov, N. et al., Oncogene, 8:1183–1193(1993); Martin, D. W. et al., J. Biol. Chem., 268:13062–13067(1993)) or the CCAAT binding factor(see: Agoff, S. N. et al., Science, 259:84–87(1993)), and inhibits the TATA-box or CCAAT-box-mediated transcription.

It has been reported that p53 is a common target of the transforming proteins of several DNA viruses, e.g., p53 associates with SV40 large T(see: Lane, D. P. and Crawford, L. V., Nature, 278:261–263(1979); Linzer, D. I. H. and Levine, A. J., Cell, 7:43–52(1979)), Adenovirus E1B(see: Sarnow, P. et al., Cell, 28:387–394(1982)), human papilloma virus E6(see: Werness, B. A. et al., Science, 248:76–79 (1990)), Ebstein Barr Virus EBNA5(see: Szekely, L. et al., Proc. Natl. Acad. Sci., USA, 90:5455–5459(1993)) and HBV X gene product(see: Feitelson, M. A. et al., Oncogene, 8:1109–1117 (1993)). These viral proteins are thought to abrogate the normal functions of p53 leading to the transformation of infected cells. In SV40 DNA replication, p53 interferes with the ability of T antigen to mediate the viral replication either by binding to replication origin(see: Bargonetti, J. et al., Cell, 65:1083–1091(1991)) or by forming complexes with T antigen(see: Friedman, P. N. et al., Proc. Natl. Acad. Sci., USA, 87:9275–9279(1990)).

Under the circumstances, the present invention have delineated the biological roles of p53 in the replication of HBV, which is a causative agent of frequently occurring acute/chronic hapatitis, liver cirrhosis and HCC.

SUMMARY OF THE INVENTION

In accordance with the present invention, the inventors tested the effects of p53 on transcription and replication of HBV under the hypothesis that p53 may work as a defense mechanism against HBV infection and discovered that: p53 inhibits the synthesis of 3.6 kb pregenomic RNA leading to the dramatic inhibition of HBV replication.

Based on the above discoveries, the inventors developed a novel inhibitor of HBV replication, which can be developed into an agent for the treatment of acute/chronic hapatitis and prevention of liver cirrhosis and HCC.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Since p53 represses the activity of several viral promoters (see: Jackson, P. et al., Oncogene, 8:589–597 (1993)), the present inventors have investigated the possibility whether p53 regulates the HBV promoter; and, it was determined that over-expression of p53 inhibits the activity of the pregenomic/core promoter as well as the HBV replication.

Two hepatoma derived cell lines, i.e., Hep G2 and Hep 3B, were employed to determine the inhibitory effect of p53 on core promoter driven transcriptional activation. Hep G2 is negative for HBV integration while positive for the presence of endogenous p53(see: Hosono, S. et al., Oncogene, 6:237–243(1991); Puisieux, A. et al., Oncogene, 8:487–490 (1993a); Puisieux, A. et al., FASEB, 7:1407–1413(1993b)); and, Hep 3B is positive for HBV integration, but is deficient in endogenous p53(see: Hosono, S. et al., Oncogene, 6:237–243(1991); Puisieux, A. et al., Oncogene, 8:487–490(1993a); Puisieux, A. et al., FASEB, 7:1407–1413 (1993b)).

The status of p53 in Hep G2 appears to be wild-type (see: Hosono, S. et al., Oncogene, 6:237–243(1991); Puisieux, A. et al., FASEB, 7:1407–1413(1993b)), even though this view is based on the SSCP(single-stranded conformation polymorphism) analysis on selected exons, leaving the possibility that the point mutation remains to be detected. Whatever the status of endogenous p53 in Hep G2 cells, over-expression of p53 led to the almost complete inhibition of core promoter activity and the same inhibitory effect of p53 was observed in p53 deficient cell line, Hep 3B, displaying that the presence of endogenous p53 in Hep G2 cells do not pose a problem in assaying the effect of exogenous p53 over-expression. Even though HBV DNA is integrated in Hep 3B, the expression of HBV-derived proteins is limited to very low level of HBsAg and X gene product is not detectable(see: Aden, D. D. et al., Nature, 282:615–616 (1979)) rendering it unlikely that the presence of integrated HBV sequence affects the analysis of the effects of p53 over-expression.

The inhibitory role of p53 on HBV replication was assessed by the reduced levels of three different markers, i.e., HBsAg and HBc/eAg secreted into the medium, HBV DNA, and RNAs. The close relationship of the pregenomic RNA level and the HBV replication has been established by others (see: Seeger, C. et al., Science, 232:477–484(1986); Will, H. et al., J. Virol., 61:904–911(1987); Yaginuma, K. and Koike, K., J. Virol., 63:2914–2920(1989); Yuh, C. H. et al., J. Virol., 66:4073–4084(1992)) pointing that the most likely mechanism for the observed inhibitory role of p53 on HBV replication is through down-regulation of the core promoter. The proportionality of the core promoter activity to the viral replication is also evidenced in the effects of mutant p53 observed in the invention. Mutant p53 expression plasmid G154V consistently displayed almost complete loss of the wild-type p53's ability while R273L retained a part of the ability, to repress the core promoter activity and the virus production. Taken together, the inventors proposed that the observed inhibition of virus production by p53 is mediated through the down-regulation of the pregenomic/core promoter.

The present invention is further illustrated in the following examples, which should not be taken to limit the scope of the invention.

EXAMPLE 1

Preparation of effector and reporter plasmids

Effector plasmids, pcDNA-p53, G154V and R273L, were prepared as follows. Human wild-type p53 expression plasmid pcDNA-p53 was created by subcloning 2.55 kb BamHI fragment of p53 cDNA(see: Zakut-Houri, R. et al., EMBO. J., 4:1251–1255 (1985)) to BamHI site of pcDNA.1 (Invitrogen, USA). Mutant p53 expression plasmids G154V and R273L were created by site directed mutagenesis. 2.55 kb BamHI fragment of p53 cDNA was subcloned into M13mp19(New England Biolabs, USA) and was mutated at amino acid position number 154 and 273 by the Kunkel's method (see: Kunkel, T. A., Proc. Natl. Acad. Sci., USA, 82:488–492(1985)), shifting GCT to GTC and CGT to CTT respectively. Oligonucleotides used in mutagenesis were CACCCCCGCCCGTCACCCGCGTC SEQ. ID. NO.: 1 for G154V and GCTTTGAGGTGCTTGTTTGTGCC SEQ. ID. NO.: 2 for R273L. The resulting p53 mutants were subcloned into pcDNA. 1 as described for pcDNA-p53 construction.

Figure 1A:
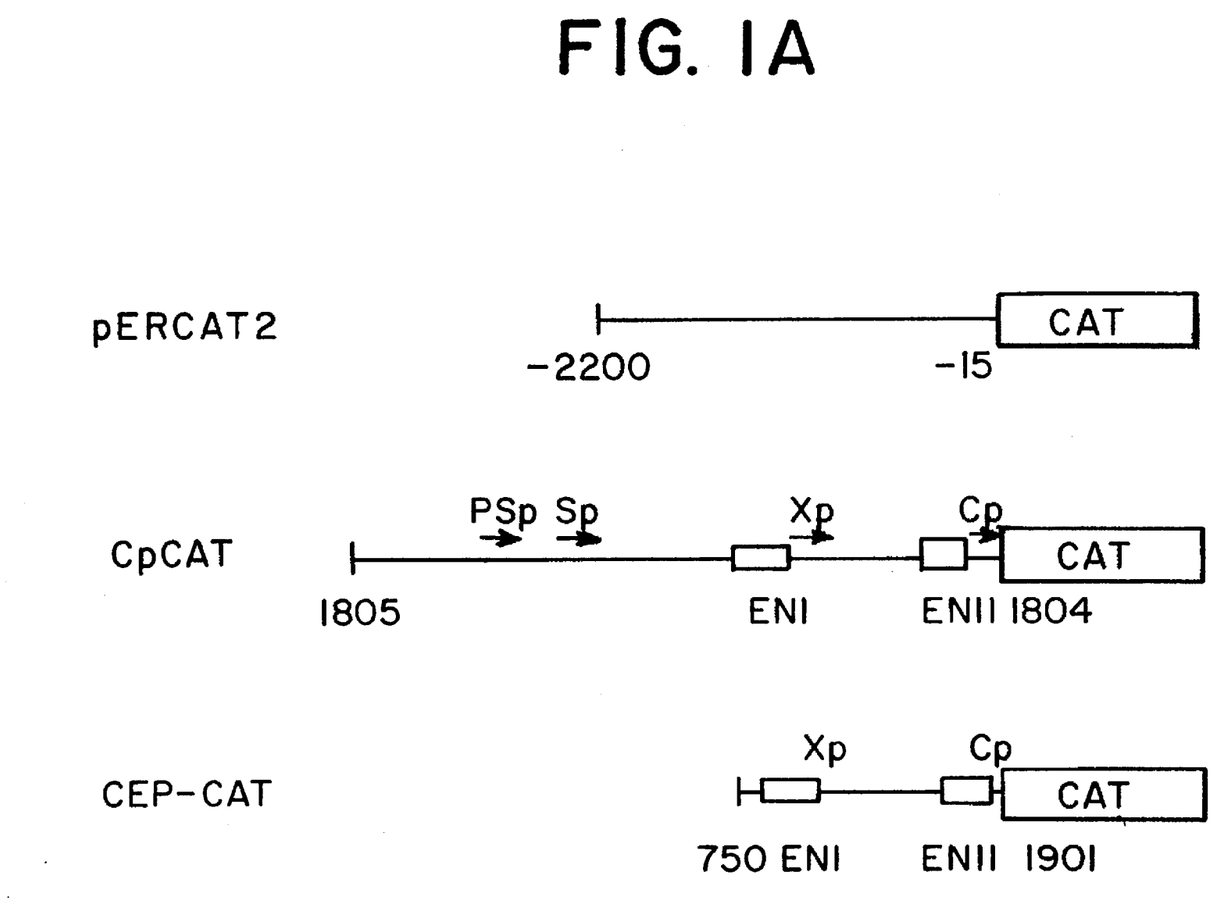
FIG. 1A depicts genetic maps of the reporter plasmids employed in the invention.

Reporter plasmids, pERCAT2, CpCAT and CEP-CAT, were prepared as follows. Control reporter plasmid pERCAT2(see: Johnson, A. C. et al., J. Biol. Chem., 263:5693–5699(1988)) carries chloramphenicol acetyltransferase (herein-after referred to as 'CAT') gene transcriptionally regulated under EGF(epidermal growth factor)-receptor promoter(see: Johnson, A. C. et al., J. Biol. Chem., 263:5693-5699(1988)). HBV core promoter linked to luciferase reporter gene, CpLUC(see: Raney, A. K. et al., J. Virol., 64:2360-2368 (1990)) was the source of CpCAT. From CpLUC, 3.2 kb HindIII fragment covering HBV genome was isolated and subcloned into HindIII site of pGEMCAT, which has the CAT gene subcloned into pGEM7Z(+)(Promega, USA). CEP-CAT was constructed by subcloning HBV sequence 750 to 1901 to Kpnl and Xbal site of pGEMCAT. Maps of the reporter plasmids are described in FIG. 1A. CpCAT bears a complete copy of HBV genome in the configuration that the expression of CAT gene is governed by the pregenomic/core promoter. In CEP-CAT, 1151 bp of core promoter region including liver specific enhancer I and II (nucleotide position 750 to 1901 of HBV genome) is placed upstream of the CAT gene. Arrows indicate the position and direction of transcription from pre-S(PS), major surface antigen(S), X-gene(X), and the core(C) promoters respectively. Nucleotide sequence numbering was adopted from the system of Wain-Hobson and Tiollais(see: Wain-Hobson, S. and Tiollais, P., in Genetics Maps, 1984). In addition, the locations of liver specific enhancer I(ENI) and enhancer II(ENII) are indicated.

EXAMPLE 2

Transfection of effector and reporter plasmids

Transfections were carried out basically after Sambrook et al.(see: Sambrook, J. et al., Molecular Cloning: a Laboratory Manual, 2nd Ed., 1989). Hep G2 cells(ATCC HB 8065) were employed for transfection unless stated otherwise. Hep G2 cells were cotransfected with 5 μg of reporter plasmids and 3 μg of effector plasmids by DEAE-dextran method: One day before transfection, $2 \times 10^5$ cells per 60 mm-diameter plate were seeded. On the day of transfection, the cells were washed twice with phosphate-buffered saline (hereinafter referred to as 'PBS') and were treated with 0.4 mg/ml of DEAE-dextran and appropriate amount of DNA cocktail made in PBS. Incubation was proceeded for 3 hrs with 0.1 mM chloroquine diphosphate at 37° C. $CO_2$ incubator humidified 70%. Subsequently, 10% of DMSO (dimethyl sulfoxide) shock was given. Transfected cells were then incubated with Dulbecco's Modified Eagle's Medium (hereinafter referred to as 'DMEM') supplemented with 10% fetal bovine serum (hereinafter referred to as 'FBS') for additional 40 hrs unless stated otherwise.

Hep 3B cells(ATCC HB 8064) were transfected by calcium phosphate coprecipitation method according to Sambrook et al., except that cells were incubated with coprecipitates for 24 hrs followed by 15% glycerol shock. Transfected cells were incubated with DMEM supplemented with 20% FBS.

EXAMPLE 3

Determination of p53 activity inhibiting pregenomic/core promoter

The effect of over-expression of wild-type p53 was investigated by employing CAT assay. CAT assay was carried out in accordance with the established protocol(see: Sambrook, J. et al., Molecular Cloning: a Laboratory Manual, 2nd Ed., 1989) with minor modifications: Incubation media of transfected cells were removed from the plates, and cells were washed twice with PBS. Then 1.4 ml of TNE(40 mM Tris (pH 7.8), 150 mM NaCl, 1 mM EDTA) was used to resuspend the cell by gentle scraping with a rubber policeman. Cells were pelleted, resuspended in 100 μl of 250 mM Tris(pH 7.8), and disrupted by 4 cycles of freeze-thawing. After centrifugation, 50 μl of supernatant was mixed with [$^{14}$C]-chloramphenicol and reactions were allowed to proceed for 2 hrs at 37° C. Reaction mix was extracted with ethyl acetate, dried and analyzed by silica gel thin layer chromatography(Cat. No. 13179, Kodak Co., USA) in 95:5 (v/v) chloroform/methanol. Spots were visualized by autoradiography and quantitated by cutting out the appropriate regions of the chromatographic plate and counting in the scintillation counter. Transfection of cells were performed in duplicates and at least three independent experiments were carried out and the results were averaged.

Figure 1B:
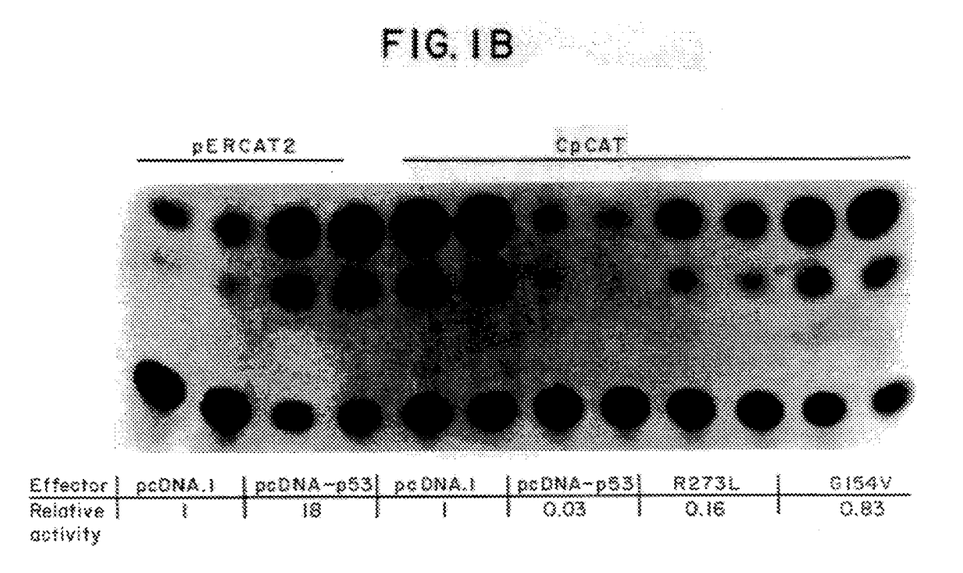
FIG. 1B is a photograph showing CAT activity of Hep G2 cells cotransfected with CpCAT reporter plasmid and p53 expression plasmids(40 hrs after transfection)

When CpCAT was employed as reporter plasmid, transfection of pcDNA-p53 repressed the core promoter activity dramatically, down to 3% of the control(see: FIG. 1B). On the other hand, two p53 mutants, R273L and G154V, reduced the CAT activity with different degree, down to 16% and 83% of the control value, displaying the specificity of the wild-type p53 action on the core promoter of HBV. In FIG. 1B, the numbers below figure represent the relative CAT activity. In contrast to the down-regulation of the core promoter by p53, the activity of control reporter, pERCAT2, was enhanced more than 18-fold by over-expression of p53. These results suggest that the observed down-regulation of core promoter by p53 is promoter-specific and, at the same time, is not caused by the general inhibition of the transcriptional machinery by p53.

Figure 1C:
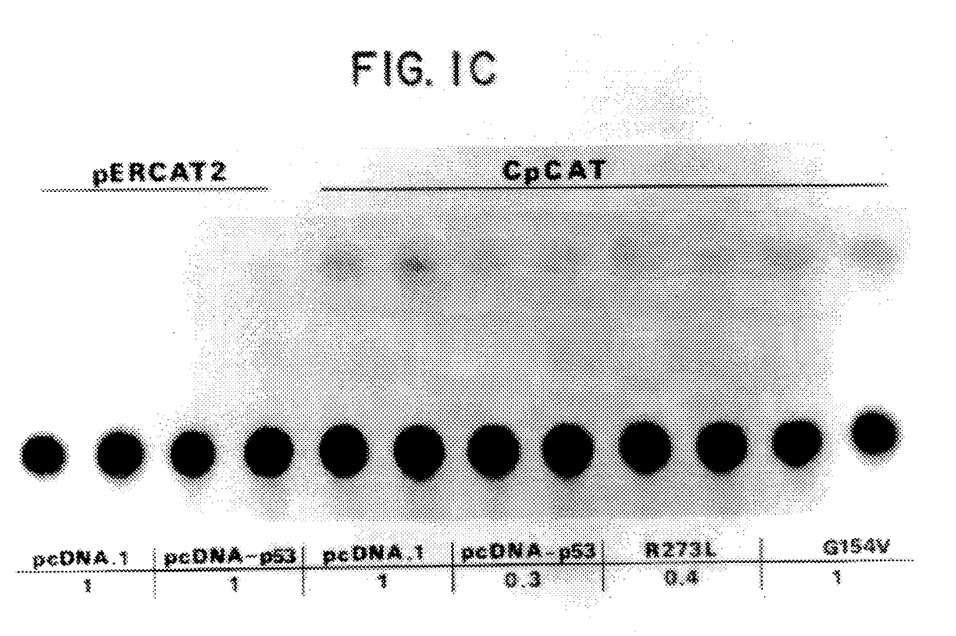
FIG. 1C is a photograph showing CAT activity of Hep G2 cells cotransfected with CpCAT reporter plasmid and p53 expression plasmids(15 hrs after transfection)

To differentiate whether the observed inhibitory effect of p53 is through p53-mediated cell cycle arrest or not, we measured the CAT activity at the earliest stage detectable after transfection(see: FIG. 1C). In FIG. 1C, the numbers below figure represent the relative CAT activity. Experiment was carried out analogously to the above said experiment except that transfected cells were harvested at the earliest stage which CAT activity was detectable, i.e., 15 hrs after transfection. The inhibitory effect of p53 was already evident at this early stage: i.e., wild-type p53 repressed core promoter-driven CAT activity down to 30% of the control, while R273L and G154V reduced the CAT activity down to 40% and 100% of the control. Although not conclusive, these results suggest that the effect of wild-type p53 on HBV core promoter is not due to the growth arrest by p53.

Figure 1D:
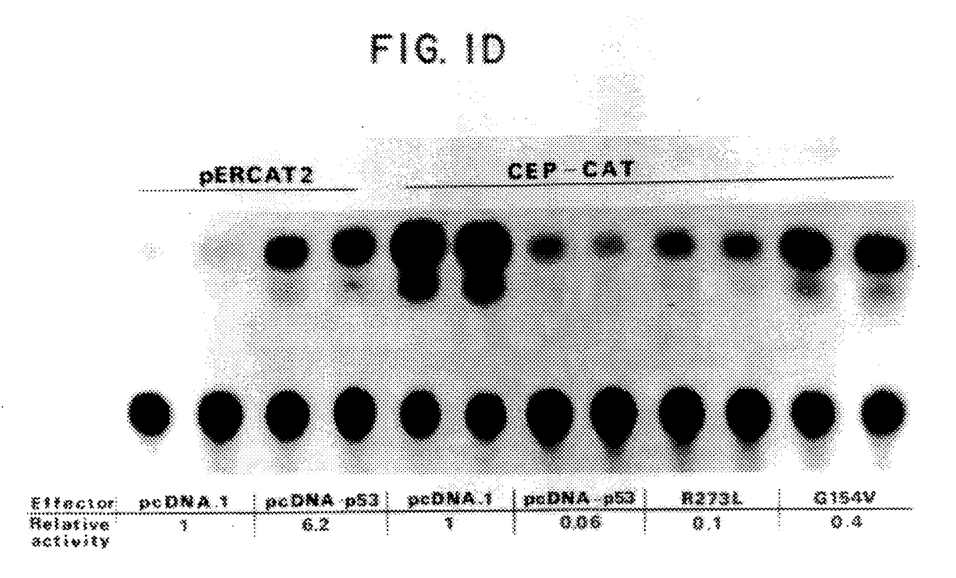
FIG. 1D is a photograph showing CAT activity of Hep G2 cells cotransfected with CEP-CAT reporter plasmid and p53 expression plasmids.

Whether a short version of the core promoter, CEP-CAT, is able to mediate the same inhibitory regulation was tested by p53(see: FIG. 1D). In FIG. 1D, the numbers below figure represent the relative CAT activity. Experiment was carried out analogously to the above said experiment except that the short version of the core promoter, CEP-CAT plasmid, was employed. CEP-CAT was regulated in an almost identical fashion by the effector plasmids as CpCAT. Wild-type p53 repressed the CAT activity, down to 6% of the control, whereas the R273L and G154V mutants reduced the activity, down to 10% and 40% of the control, respectively. Therefore, it is suggested that the sequence responsible for the down regulation of core promoter be contained in the 1.15 kb region of HBV genome between 750 to 1901.

Figure 2:
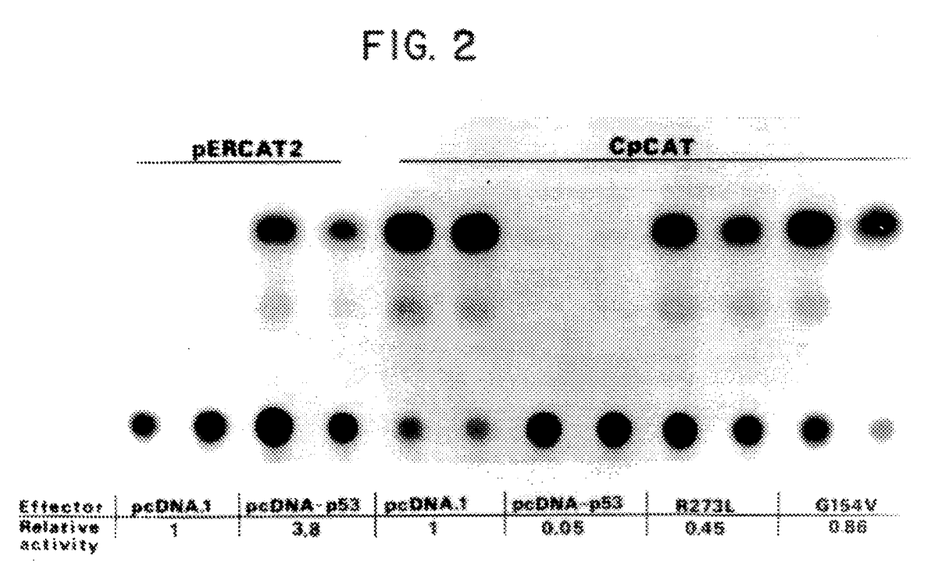
FIG. 2 is a photograph showing CAT activity of Hep 3B cells cotransfected with CpCAT reporter plasmid and p53 expression plasmids.

As already stated, Hep G2 cells retain endogenous p53 and it can be argued that the observed phenomenon is due to the effect of endogenous p53 associated with exogenous p53, whatever the status of p53 in Hep G2 cells would be. To assay the p53 effect without interference by endogenous p53, an analogous experiment to the above said was carried out except that p53-deficient cell line, Hep 3B was employed instead of Hep G2 cell line, employing CpCAT as a reporter (see: FIG. 2). In FIG. 2, the numbers below figure represent the relative CAT activity. The CAT activity obtained on transfection of pcDNA-p53, R273L and G154V were 5%, 45%, and 86% of the control CAT activity, respectively. Taken together, it was concluded that the activity of pregenomic/core promoter of HBV is repressed specifically by wild-type p53 and this effect is not due to the general inhibition of the transcriptional machinery.

EXAMPLE 4

Determination of p53 activity repressing the replication of HBV(I)

Figure 3A:
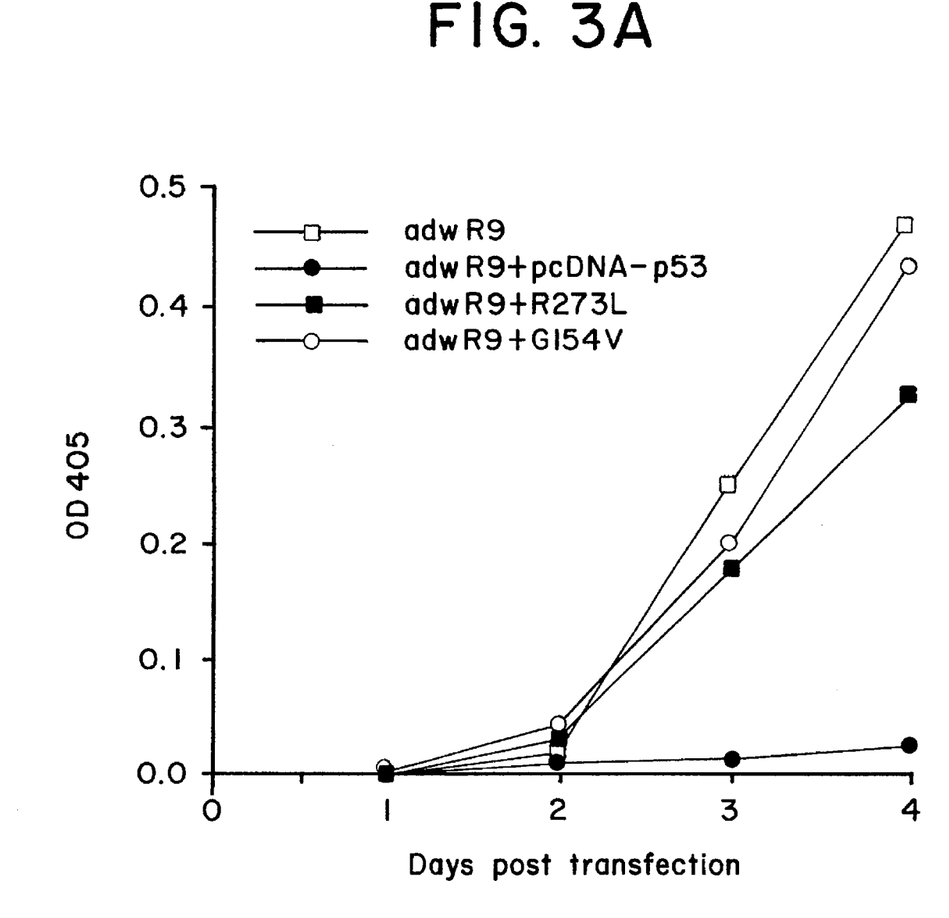
FIG. 3A is a graph teaching inhibition of HBsAg production by the expression of wild-type p53.
Figure 3B:
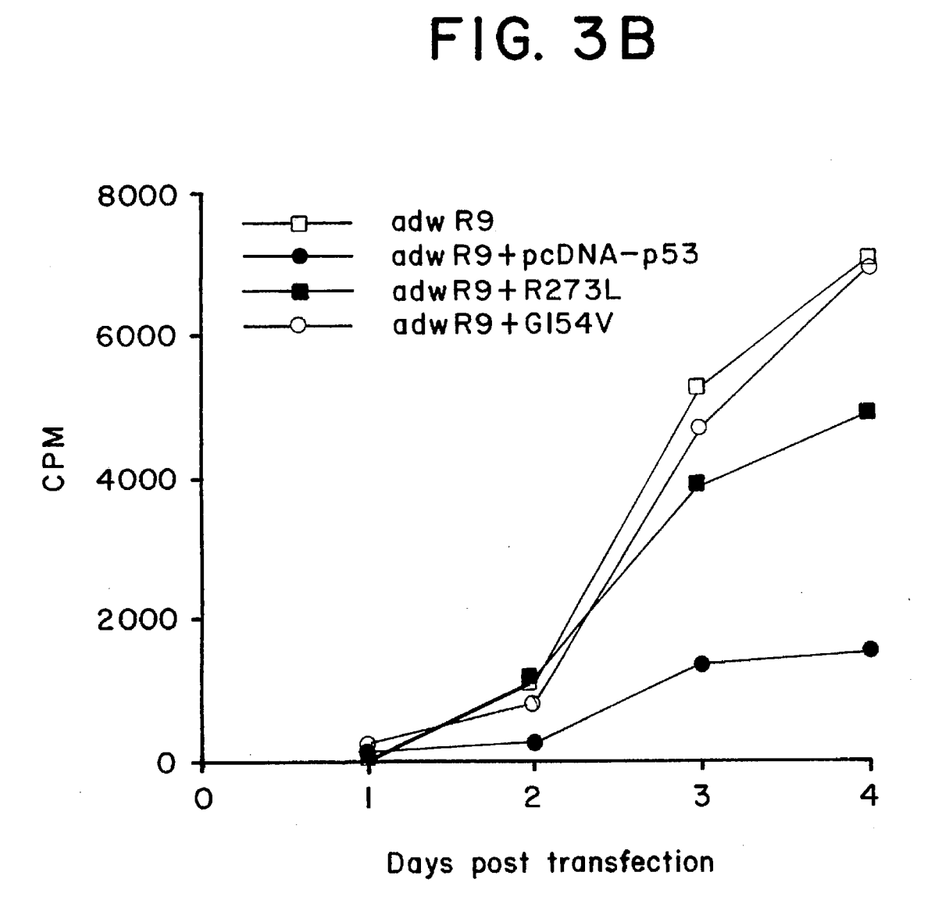
FIG. 3B is a graph teaching inhibition of HBc/eAg production by the expression of wild-type p53.

To verify whether the p53 have an inhibitory role in the replication of HBV by reducing the level of pregenomic RNA or not, adw R9(see: Blum, B. E. et al., J. Virol., 66: 1223-1227(1992)), the plasmid containing a head-to-tail dimer of HBV DNA, was transiently transfected into Hep G2 cells along with the p53 expression plasmids. Effect of p53 on HBV replication was assayed by counting the levels of surface antigen(HBsAg) and the core protein(HBc/eAg) secreted into the culture medium, in accordance with Blum et al.'s method. From the transfected cells, one ml of the culture medium was taken daily for assay and replaced by same amount of fresh media. The surface antigen(HBsAg) released into the culture medium was measured by the aid of an enzyme-linked immunoassay employing Genedia-S. M.(Korea Green Cross Co., Korea). Core-related antigens (HBcAg and/or HBeAg) were detected by the aid of the HBc/eAg radioimmunoassay employing Abott HBe diagnosis kit(Abott Diagnostic Systems, USA). To quantify the viral antigens proportionally, the assays were performed over linear range of the kits; media were diluted to either 1:50 for HBsAg EIA or 1:10 for HBc/eAg RIA. Experiments were carried out in duplicates and were repeated at least 4 times for each point. The data presented in FIGS. 3A and 3B is obtained from a single representative experiment.

In adw R9 transfected set, HBsAg was not detectable on day 1 post transfection(see: FIG. 3A). Starting from day 2, continuously increasing amounts of HBsAg were secreted into the medium. In contrast, cotransfection of pcDNA-p53 resulted in the dramatically reduced levels of HBsAg(95% reduction on day 3 post transfection). This observation was specific for wild-type p53, since cotransfection of the plasmids encoding two p53 mutants resulted in the different degree of the levels of HBsAg(40% reduction for R273L and only 10% reduction for G154V on day 3 post transfection). It was determined that the degree of reduction in HBsAg level by R273L was more significant compared to that by G154V. The time dependent alteration in levels of HBc/eAg displayed the similar pattern to that of HBsAg(see: FIG. 3B). Cotransfection of pcDNA-p53 resulted in marked reduction in HBc/eAg level(80% reduction on day 3 post transfection), whereas the R273L and G154V mutants affected the HBc/eAg level slightly(30% reduction for R273L and 10% reduction for G154L on day 3 post transfection). It was also determined that the degree of reduction in HBc/eAg level by R273L was greater compared to that by G154V. The authenticity of secreted particles was assessed by CsCl density gradient centrifugation of the spent culture media and subsequent analysis of each fraction as reported by others(see: Yaginuma, K. et al., Proc. Natl. Acad. Sci., USA, 84:2678-2682(1987)). The major peaks of HbsAg or HBc/eAg were observed at 1.15 g/ml or 1.35 g/ml respectively, which is identical to previously reported by Yaginuma et al.

The behavior of p53 effector plasmids observed in this replication assay was consistent with that from the CAT assay described in Example 3: that is, over-expression of wild-type p53 markedly inhibited the pregenomic/core promoter activity as well as the viral antigen production, and R273L retained a part of the inhibitory effect, while G154V completely lost the ability.

EXAMPLE 5

Determination of p53 activity repressing the replication of HBV(II)

Activity of p53 on viral replication was further assessed by quantifying the HBV DNA level after cotransfection of adw R9 and pcDNA-p53 plasmids. Viral DNA levels were analyzed both from cellular extracts and culture media three days after transfection by Southern hybridization.

DNA preparation was performed in accordance with the method known in the art(see: Yaginuma, K. et al., Proc. Natl. Acad. Sci., USA, 84:2678-2682(1987)) with slight modification. For analysis of DNA in cell lysates, transfected cells were collected 3 days after transfection and suspended in hypotonic buffer(20 mM Tris(pH 7.5), 100 mM NaCl, 1 mM EDTA, 0.5% NP-40). After homogenization, 10 mM of $MgCl_2$ and 23 units/ml of DNase 1 were added and incubated at 37° C. for 3 hrs, followed by centrifugation at 5,000 rpm for 1 hr. The supernatant was layered over 30% sucrose solution in TNE and centrifugation at 35,000 rpm for 12 hrs at 4° C. The resulting pellet was resuspended in proteinase K digestion buffer(200 mM Tris(pH 7.8), 25 mM EDTA, 300 mM NaCl, 2% SDS, 400 µg/ml proteinase K) and incubated at 56° C. for 3 hrs. The digested sample was phenol/chloroform extracted twice and ethanol precipitated. For analysis of DNA in spent culture medium, virus particles secreted into the culture medium were concentrated and loaded onto 30% sucrose solution in TNE and treated as described above.

Figure 4A:
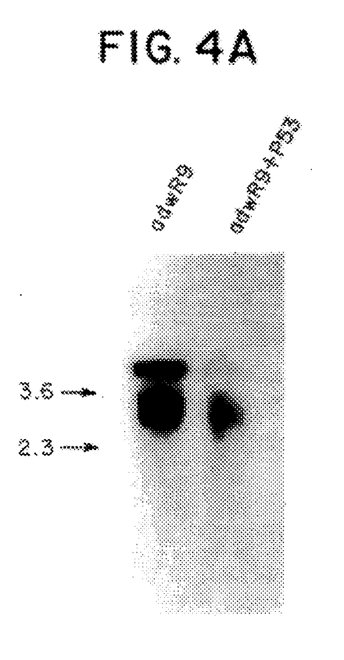
FIG. 4A is a photograph showing Southern blot analysis performed on viral DNA isolated from cell lysate upon p53 expression.
Figure 4B:
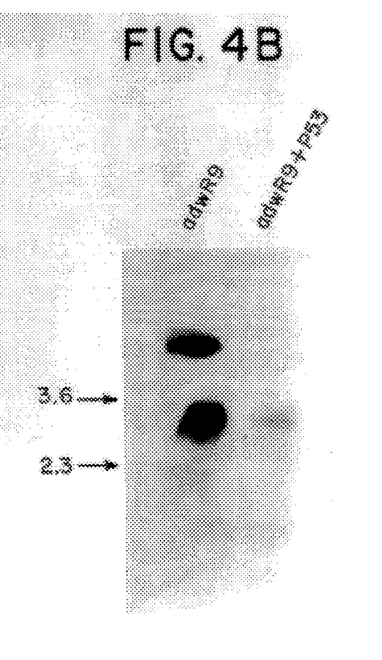
FIG. 4B is a photograph showing Southern blot analysis performed on viral DNA in culture medium upon p53 expression.

For Southern blotting, above prepared DNAs from cell lysate and culture medium were run on 1.5% agarose gel. The amount of DNA loaded on each lane was equivalent of that from a 60 mm diameter plate. The gel was depurinated in 0.25N HCl for not more than 6 minutes, followed by direct transfer to Gene Screen Plus in 0.4N NaOH for 16 hrs. Hybridization was performed in 6×SSC, 0.1% SDS, 50% formamide, 10% Dextran sulfate and 100 µg/ml of denatured salmon sperm DNA at 42° C. using [$^{32}$P]-labelled adw R9 as a probe. The levels of HBV DNA both in cell extract(see: FIG. 4A) and in the media(see: FIG. 4B) were determined.

In FIGS. 4A and 4B, lane 'adw R9' represents HBV DNA level in case of transfection of adw R9 only, and lane 'adw R9+p53' represents HBV DNA level in case of cotransfection of adw R9 and pcDNA-p53 plasmids. As can be seen in FIGS. 4A and 4B, it was determined that the levels of HBV DNA both in cell extract and in the media were reduced more than 90% when pcDNA-p53 was cotransfected, supporting the earlier conclusion that p53 is a potent inhibitor of HBV replication.

EXAMPLE 6

Determination of p53 activity repressing the replication of HBV(III)

Figure 5A:
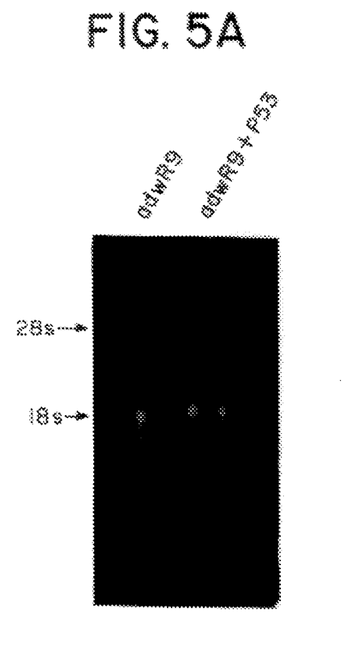
FIG. 5A is a photograph showing total cellular RNAs isolated from cell lysate upon p53 expression.
Figure 5B:
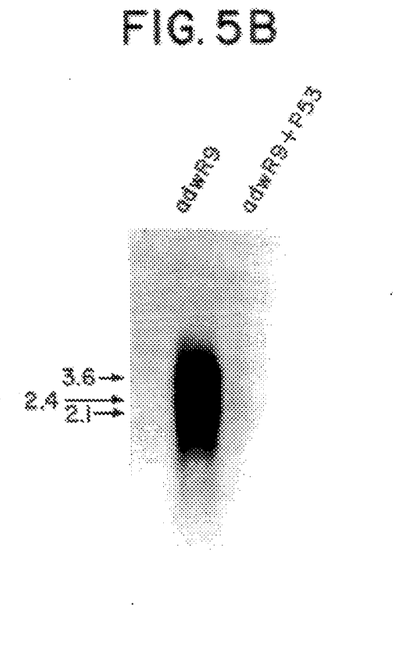
FIG. 5B is a photograph showing Northern blot analysis of HBV transcripts upon p53 expression.

Activity of p53 on viral replication was further assessed by quantifying the HBV RNA level after cotransfection of adw R9 and pcDNA-p53 plasmids. Total RNAs were isolated from Hep G2 cells transfected with adw R9 only or adw R9 plus pcDNA-p53 as described(see: Sambrook, J. et al., Molecular Cloning: a Laboratory Manual, 2nd Ed., 1989). After homogenizing the cells in 6M guanidine isothiocyanate, 0.5% sarcosyl, and 1 mM β-mercaptoethanol, the cell lysate was loaded onto 3 ml of 5.7M CsCl in 1 mM EDTA cushion and centrifuged at 35,000 rpm at 20° C. for 24 hrs. The RNA pellet was resuspended in RNase free water, followed by ethanol precipitation with 0.3M sodium chloride(pH 5.0). 30 μg of the total RNA was loaded onto 2.2M formaldehyde denaturing gel and stained. Staining of the gel displayed that the level of total RNAs loaded on each lane was equal(see: FIG. 5A). In FIGS. 5A and 5B, lane 'adw R9' represents RNA level in case of transfection of adw R9 only, and lane 'adw R9+p53' represents RNA level in case of cotransfection of adw R9 and pcDNA-p53 plasmids. The levels of HBV RNAs were determined by Northern blot hybridization with [$^{32}$P]-labelled adw R9 DNA as a probe. The gel in FIG. 5A was transferred to Gene Screen Plus(DuPont, USA) with 10×SSC and probed with labelled adw R9 HBV DNA. The probe detected the 3.6 kb pregenomic RNA as well as the 2.4 and 2.1 kb RNA species. It was determined that cotransfection of pcDNA-p53 resulted in more than 95% reduction of all the viral transcripts level(see: FIG. 5B), again supporting the idea that the p53 acts as a repressor of HBV replication.

Based on the above results, it was concluded that wild-type p53 inhibits the replication of HBV by down-regulation of the pregenomic/core promoter.

EXAMPLE 7

Determination of target-specificity of p53

Figure 6A:
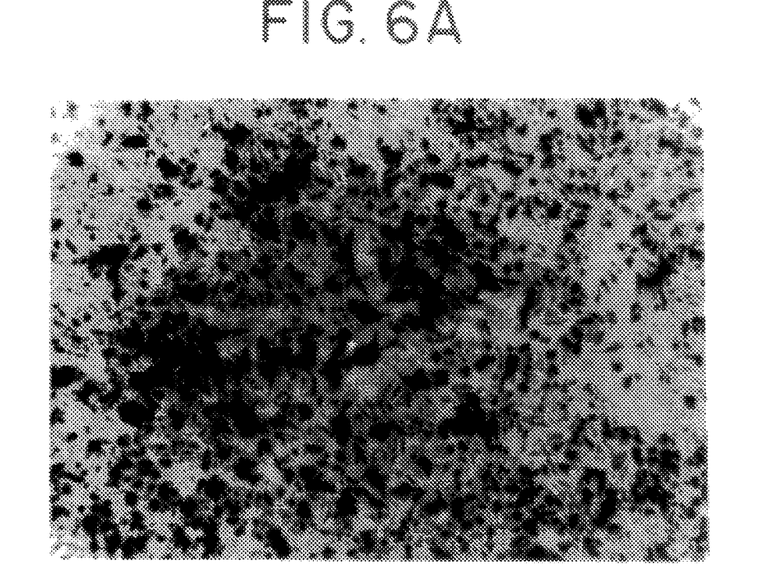
FIG. 6A is a photograph showing Hep G2 cells transformed with adw R9 and pER-βGAL.
Figure 6B:
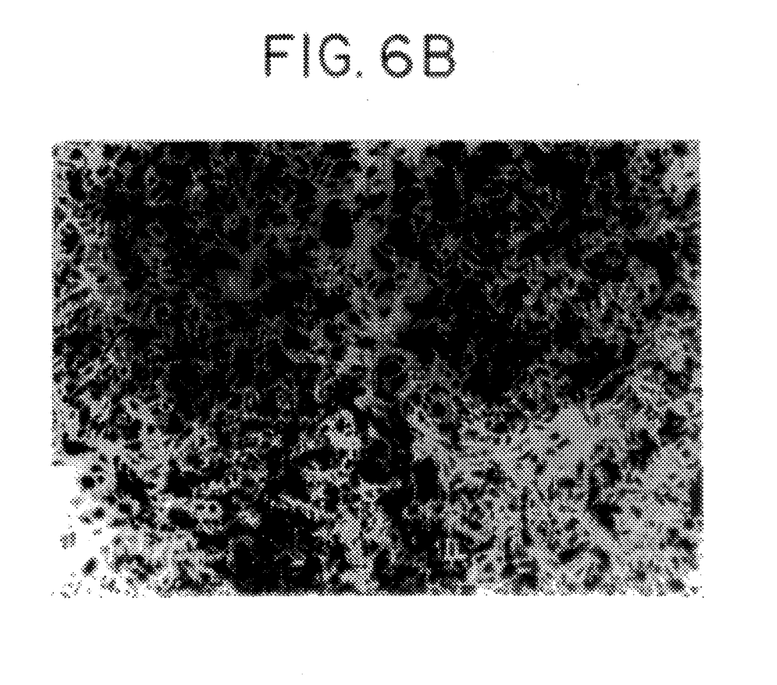
FIG. 6B is a photograph showing Hep G2 cells cotransfected with adw R9 and pcDNA-p53 plasmids, employing pER-βGAL as a reporter plasmid.
Figure 7A:
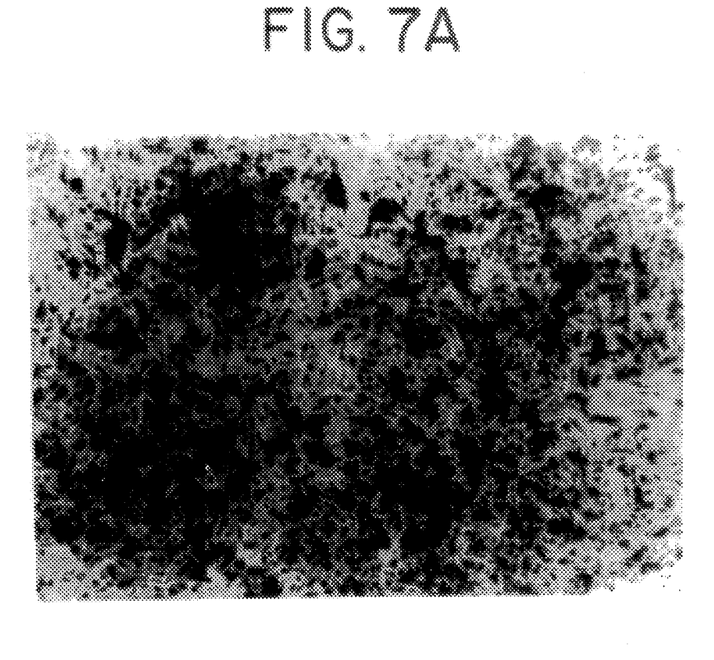
FIG. 7A is a photograph showing Hep G2 cells transformed with adw R9 and RSV-βGAL; and, FIG. 7B is a photograph showing Hep G2 cells cotransfected with adw R9 and pcDNA-p53 plasmids, employing RSV-βGAL as a reporter plasmid.
Figure 7B:
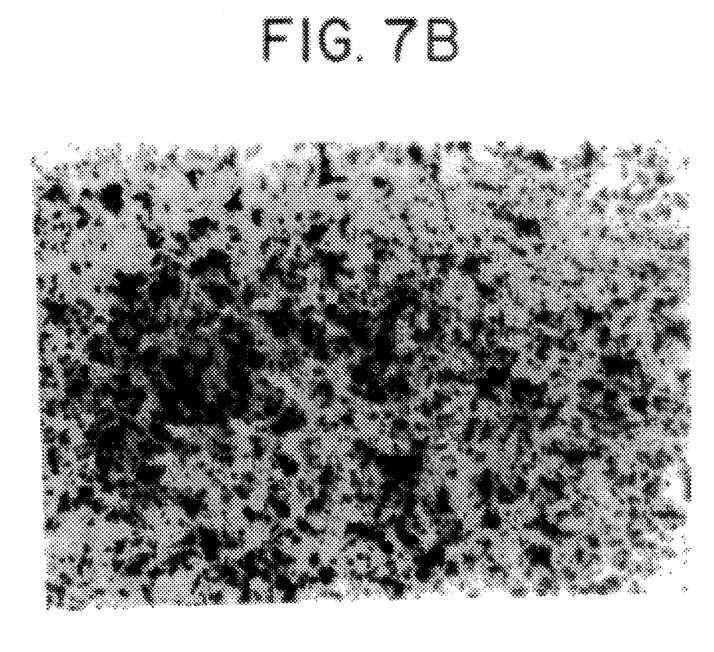

To further assess that the p53-mediated repression of HBV replication is not due to the reduction in the number of viable, transfected cells or the abberation in transcriptional machinery caused by over-expression of p53, β-galactosidase was employed as a reporter. pER-βGAL was created by subcloning 2.2 kb XhoI fragment of pERCAT2 to pNASS-β(Clonetech., USA), and therefore, pER-βGAL contains β-galactosidase gene under the control of EGF-receptor promoter. pER-βGAL was transfected into Hep G2 cells along with adw R9+/−pcDNA-p53 plasmids and the cells were subjected to histochemical staining on day 3 post transfection(see: FIGS. 6A and 6B). A plasmid, RSV-βGAL containing β-galactosidase gene under the control of RSV (Rous sarcoma virus) promoter(See: Gorman et al., Proc. Natl. Acad. Sci., USA, 79:6453(1982)) was transfected into Hep G2 cells along with adw R9+/−pcDNA-p53 plasmids and the cells were subjected to histochemical staining on day 3 post transfection(see: FIGS. 7A and 7B). Histochemical staining was performed according to the established method (See: Sanes, J. R. et al., Embo. J., 5: 3133–3142(1986)). After staining, the number of positively stained cells in the same area(5 mm$^2$) was counted at 50×magnification under the light microscope. The experiments were performed in duplicates and repeated three times. FIGS. 6A and 7A represent control(non-transformed) Hep G2 cells and, FIGS. 6B and 7B represent that transformed with pcDNA-p53, respectively. Photographs were taken at 10×10 magnification. The number of blue-color stained cells in the same area was identical whether pcDNA-p53 was cotransfected or not, indicating that the expression of p53 do not affect the number of viable, transfected cells. Furthermore, examination of the p53 transfected cells under the microscope showed no difference in morphology.

As clearly illustrated and demonstrated as aboves, the present invention provides a novel use of p53 as a HBV replication inhibitor which can be developed into an agent for the treatment of acute/chronic hapatitis and prevention of liver cirrhosis and HCC caused by HBV.

What is claimed is:

1. A method for inhibiting hepatitis B virus (HBV) replication in a cell in vitro, comprising contacting the genome of said HBV with human p53 protein.

2. The method of claim 1, wherein said cell is a hepatocyte.

3. The method of claim 1, wherein said p53 protein is expressed from a recombinant gene.

* * * * *